United States Patent [19]

Royse et al.

[11] Patent Number: 4,559,120

[45] Date of Patent: Dec. 17, 1985

[54] AGAROSE GEL ELECTROPHORESIS TECHNIQUE FOR THE DETERMINATION OF AMYLASE ISOENZYMES

[75] Inventors: Vicki L. Royse, Elmhurst; Donald M. Jensen, Oak Park, both of Ill.

[73] Assignee: Rush-Presbyterian-St. Luke's Medical Center, Chicago, Ill.

[21] Appl. No.: 478,506

[22] Filed: Mar. 23, 1983

[51] Int. Cl.[4] .................. G01N 27/26; B01D 15/08
[52] U.S. Cl. .................. 204/182.8; 201/299 R; 252/315.3; 435/22; 436/806
[58] Field of Search ............ 204/180 G, 299 R; 23/230 B; 435/22, 814; 436/806; 252/315.3

[56] References Cited

U.S. PATENT DOCUMENTS

| | | | |
|---|---|---|---|
| 3,497,437 | 2/1970 | Louderback et al. | 204/180 G |
| 3,527,712 | 9/1970 | Renn et al. | 204/180 G |
| 3,687,833 | 8/1972 | Parcells et al. | 204/180 G |
| 3,912,610 | 10/1975 | Lou | 204/180 G |
| 3,998,696 | 12/1976 | Yomoto et al. | 435/202 |
| 4,030,995 | 6/1977 | Starkweather | 204/180 G |
| 4,209,372 | 6/1980 | Bluestein et al. | 204/180 G |
| 4,246,084 | 1/1981 | Gurske | 204/180 G |
| 4,454,161 | 6/1984 | Okada et al. | 426/549 |

FOREIGN PATENT DOCUMENTS

| | | | |
|---|---|---|---|
| 0870180 | 5/1971 | Canada | 204/180 G |
| 0681362 | 8/1979 | U.S.S.R. | 204/180 G |

OTHER PUBLICATIONS

Pierre Leclerc and Jean-Claude Forest, *Clinical Chemistry*, vol. 28, No. 1, 1982.

Primary Examiner—Andrew H. Metz
Assistant Examiner—Terryence Chapman
Attorney, Agent, or Firm—Fitch, Even, Tabin & Flannery

[57] ABSTRACT

Separation of all clinically relevant isoamylase bands including $P_1$ $P_{1b}$, $P_2$, $P_3$, $P_4$, $S_1$, $S_2$, $S_3$, $S_4$ and $S_5$ is achieved in a test in which a biological sample is electrophoresed on an agarose gel supporting a tris-sodium barbital-barbital buffer at a pH of between 8.4 and 9.2. The barbital anion concentration is between about 0.03 and about 0.08 M, the tris cation concentration is between about 0.03 M and about 0.07 M; and the sodium cation concentration is between about 0.03 M and about 0.07 M. Agarose is present in the gel at concentrations of between about 0.4 and about 1.5 weight percent.

14 Claims, 1 Drawing Figure

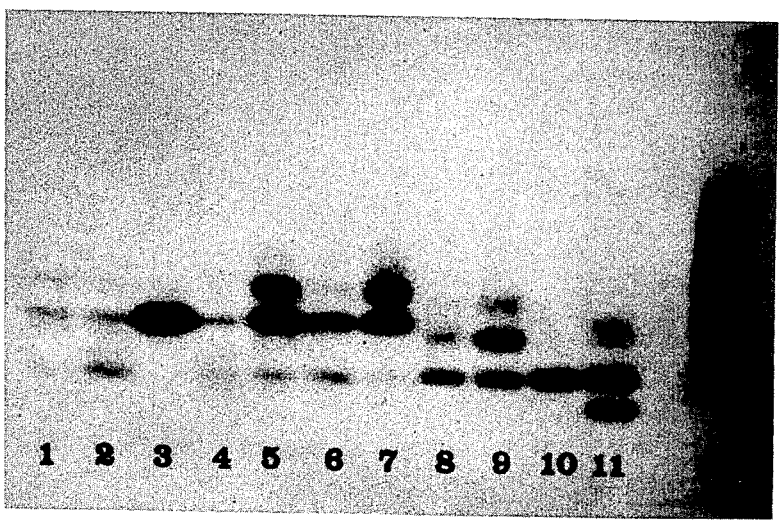

AGAROSE GEL ELECTROPHORESIS TECHNIQUE FOR THE DETERMINATION OF AMYLASE ISOENZYMES

The broad term "amylase" refers to enzymes that catalyze the hydrolysis of starch and glycogen. Amylase is distributed throughout the human body and can be detected in numerous body fluids, such as blood serum, urine, peritoneal fluid, and saliva. Amylase levels in fluids can be determined by assays in which a colored dye is released and expressed upon amylase-catalyzed hydrolysis of a starch.

Amylase found in the body consists not of a single enzyme but rather includes several enzymes having different structures but which perform substantially the same function and are referred to as isoenzymes of amylase or isoamylases. Broadly, there are two types of isoamylases, salivary(S) and pancreatic(P); however, each of these two classes include several isoenzymes which differ in certain properties. The different isoamylases can be distinguished according to their electrophoretic mobilities.

A variety of pathologic conditions give rise to elevated amylase levels which can be detected in blood serum, urine and other body fluids. Because elevated amylase is strongly indicative of a pathological condition, an assay revealing elevated total amylase is generally followed up by more comprehensive investigation in an attempt to diagnose the cause of the elevated amylase, and substantial medical costs are incurred investigating the causes of elevated amylase levels.

Because various pathologic conditions which give rise to elevated total amylase levels do not affect the levels of all isoenzymes equally, knowledge of the respective levels of the various isoamylases contribute significantly to defining the cause of an elevated amylase level. While a number of investigators have demonstrated widely divergent amounts of the isoamylases in patients with various conditions, the results of such investigations have not been generally applied in clinical testing. Previously described electrophoretic techniques have not been adapted for clinical testing and have not sufficiently separated all significant isoamylase bands desirable for unambiguous interpretation of results. An example of a previously reported electrophoresis protocol is in P. Leclerc et al., Clin. Chem. 28, n.1 37–40, 1982; however, identification of certain isoamylase bands, i.e., the $P_{1b}$ and $S_5$ bands, is not reported.

A clinical test for isoamylase is commercially sold under the tradename Phadebas ® Isoamylases Test by Pharmacia Diagnostics. This test only provides levels of salivary isoamylase and pancreatic isoamylase and is performed by assaying for total isoamylase (salivary plus pancreatic) while performing a simultaneous assay for amylase in the presence of an inhibitor that supresses activity of the salivary isoamylases but has little inhibitory effect on the pancreatic isoamylases.

It would be desirable to have an electrophoresis protocol which would clearly separate substantially all of the isoamylases for which diagnostic significance is attributed to their presence or absence and/or to their respective levels. It would be further desirable to provide such an electrophoresis protocol which is easily and reliably performed in a clinical laboratory and which may be adapted to be supplied as a prepackaged test kit.

SUMMARY OF THE INVENTION

The present invention provides an agarose gel electrophoresis system which is performable on relatively small test plates and which provides clear, distinct separation of the $P_1$, $P_{1b}$, $P_2$, $P_3$, $P_4$, $S_1$, $S_2$, $S_3$, $S_4$, and $S_5$ bands. The support medium is agarose, and the buffer is tris-sodium barbital-barbital at a barbital anion concentration of between about 0.04 and about 0.08 M and a pH of between about 8.4 and about 9.2. The concentration of tris is between about 0.03 M and about 0.07 M and the concentration of sodium is between about 0.03 M and about 0.07 M. The electrophoresis plates are backed by a cooling block that is maintained at a temperature of between about 2° C. and about 25° C. as the gels are subjected to between about 50 volts and about 400 volts, causing differential migration of the isoamylases.

IN THE FIGURE

The FIGURE is a photograph of an actual electrophoresis performed in accordance with the present invention, the various isoamylase bands being indicated.

DETAILED DESCRIPTION OF THE PREFERRED EMBODIMENTS

In accordance with the invention, a protocol is provided in which biological samples, such as blood sera, are electrophoresed on agarose gel using a tris-sodium barbital-barbital buffer at basic pH's. The electrophoresis plate is then exposed to a chemical system including a starch or similar substance that hydrolyzes in the presence of amylase, developing a dye which stains the gel in the region of the isoamylase bands. The electrophoresis separates the $P_1$, $P_{1b}$, $P_2$, $P_3$, $P_4$, $S_1$, $S_2$, $S_3$, $S_4$, and $S_5$ bands. Separation of the bands is effected within a relatively short running distance, permitting short length electrophoresis plates to be used. At running voltages of between about 50 and 400, separation is complete within about one half to about six hours. The small size of the plates and the stable nature of the agarose gel support provides that the electrophoresis plates might be prepared in advance and sold as components of prepackaged clinical test kits. The relatively short running time of the electrophoresis, i.e., within the working day of a clinical technician, enhances its applicability to performance in the clinical laboratory.

A significant factor in achieving the excellent separation of isoamylase bands is the selection of a buffer system. The tris-sodium barbital-barbital buffer system is not in itself unique, and related buffer systems, including sodium barbital buffers, have been used previously to electrophoretically separate isoamylase. However, this is the first use of a tris-sodium barbital-barbital buffer system for isoamylase electrophoresis and, surprisingly and unexpectedly, it is found that a tris-sodium barbital-barbital buffer gives a substantially improved separation relative to a sodium barbital buffer, such as that reported by Leclerc et al., supra. This improved separation results in an electrophoresis pattern in which substantially all clinically significant bands, including $P_{1b}$ and $S_5$, are each clearly distinguished.

Specifically, the tris-sodium barbital-barbital buffer in accordance with the present invention comprises barbital anion at a concentration of between about 0.04 and about 0.08 M. The concentration of the tris (2 amino-2-hydroxymethyl-1,3-propanediol) cation is between about 0.03 and about 0.07 M; the concentration of the sodium cation is between about 0.03 and about 0.07 M, the molar ratio of tris to sodium being between about 0.5:1 and about 2:1. Calcium lactate may be added to reduce endosmosis; calcium ion may be present in concentrations from 0 to about 0.002 M and lactate may be present in concentrations from 0 to about 0.002 M. The pH of the solution is adjusted to between about 8.4 and about 9.2 and preferably to between about 8.7 and about 8.9.

The support medium is agarose, which is preferably present at a concentration of between about 0.4 and about 1.5 weight percent of the gel (agarose plus buffer) and more preferably about 1.0 weight percent. The usual method of preparing electrophoresis support plates is to suspend agarose in the buffer, heat the buffer with the suspended agarose until the agarose dissolves and pour the agarose-in-buffer solution on a sheet or plate of backing material. Preferably, the agarose-in-buffer solution is degassed while still at elevated temperatures and before it is poured. The dissolved, degassed agarose-in-buffer solution is poured to a thickness between about 0.5 and about 2 mm and allowed to cool, thereby gelling. As an alternative means of providing a gel with the proper buffer, an agarose gel may be made with water or other buffer system, and the gel soaked in the tris-sodium barbital-barbital buffer for a time period that is sufficiently extensive for the tris-sodium barbital-barbital buffer to replace the water or other buffer.

Samples presumably containing isoamylases are applied to the gel along side of one or more controls which should collectively provide all of the relevant isoamylase bands for visual comparison. The amount of sample to be applied is determined by the total amount of isoamylases expected to be present in the unknown sample so that clear staining of each band is possible without the bands blurring together. For a gel about 1 mm or less thick, it is preferred to apply between about $5 \times 10^{-4}$ and about $4 \times 10^{-2}$ IU (one IU of amylase being defined as the amount of enzyme that will catalyze the hydrolysis of 1 $\mu$Mol. of glucosidic linkages per minute at 37° C.) of total amylase per cm of band length (in the direction transverse to the running direction). For a blood serum sample, this will typically correspond to approximately 2 $\mu$l/mm of band length, although if the amylase is known to be extremely elevated, a clearer pattern may be obtained using proportionately less sample (or a diluted sample).

The electrophoresis voltage should be sufficient to effect quick separation, both for reasons of time efficiency and so that diffusion of the bands is limited relative to electrophoretic migration; however, the voltage should not be so high that it denatures the isoamylases. The electrophoresis voltage is also limited by the efficiency of the cooling system for the gel and must not produce heat in the gel that cannot be dissipated by the cooling system sufficiently to maintain the gel at temperatures below where the gel destabilizes and/or the isoamylases denature. Generally, isoamylase electrophoreses will be run at between about 50 and about 400 volts.

To dissipate the heat that is developed in the gel as a result of that current, it is preferred that the backing material that carries the gel be in surface contact with a cooling block that is maintained at a temperature of between about 2° C. and about 25° C. It is understood that temperatures within the gal will be somewhat higher, but contact of a cooling block with substantially the entire surface of the backing plate is generally sufficient to maintain localized gel temperatures within acceptable upper limits.

A suitable electrophoresis apparatus for effecting the separation is sold under the tradename Panagel by Worthington. Using this apparatus, hot agarose in buffer solution is poured onto a backing sheet of material, e.g., Mylar, or other flexible plastic and allowed to cool and gel. The gel and backing material are deformed along a convex cooling block with the ends of the gel dipping into the tris-sodium barbital-barbital buffer contained in chambers along both ends of the cooling block.

Using the buffer system according to the present invention, the $S_1$, $P_3$, $S_2$, $P_4$, $S_3$, $S_4$, and $S_5$ bands migrate toward the anode, the $P_1$ and $P_{1b}$ bands migrate toward the cathode and the $P_2$ band remains close to the point of application.

The precise running time required to obtain full separation depends on factors such as voltage and thickness of the gel. Preferably the current is adjusted so that separation is complete within about one half to about 6 hours and preferably less than about 3 hours.

After the run is complete, the gels are stained using a chemical system which reacts in the presence of amylase developing a dye that colors the gel where the reaction occurs, i.e., at the isoamylase bands. Commercially available dye systems, such as Phadebas amylase tablets sold by Pharmacia Diagnostic are available for this purpose. These tablets include a dye, such as a triazine derivative, bound to starch, and the dye is released to express a visible color upon amylase-catalyzed starch hydrolysis.

The invention will now be described in greater detail by way of example.

EXAMPLE 5.77 g of tris barbital, 2.47 g barbital, 9.74 g sodium barbital and 0.28 g calcium lactate are dissolved in 0.9 L of deionized water. The pH is adjusted to 8.8 and the volume is brought to one liter.

2.5 grams of electrophoretic grade agarose (Bio-Rad) are suspended in 250 ml. of the buffer and the suspension is heated with stirring to boiling, dissolving the agarose. The agarose is immediately degassed with a vacuum pump.

A 6"×10" sheet of 0.18 thick clear polyester-based plastic film, sold under the trademark Gel Bond by Bio-Rad, is cut and placed on a level glass plate warmed to 56° C. 1 mm thick spacing discs are placed on each side of the film, approximately 35 ml of the hot agarose solution is poured between spacers, and a second glass plate is placed over the gel. The gel is allowed to cool undisturbed overnight, and then the glass plates are removed.

An area approximately 1.3 cm wide around a sample line is blotted twice for about 30 seconds each time with strips of Whatman #1 filter paper. A sample template is then placed over this area, and air bubbles are removed by touching the gel with a tissue. The template provides slots approximately 10 mm long (in the direction transverse to the running direction) and about 1 mm wide.

In each slot is applied approximately 20 $\mu$l of blood serum, each sample being applied about 5 seconds apart. The sample slots are covered, and the samples are allowed to soak into the gel for about 12 minutes. At the end of the application time, excess sample (that not diffused into the gel) is removed by blotting with a strip of filter paper.

The samples are placed on the convex cooling block of a Worthington migration unit which is cooled to 4° C. The buffer chambers are each filled with 500 ml of the tris-sodium barbital-barbital buffer. The voltage on the power unit is set for 200 volts, and a timer is set to run the electrophoresis for two hours and thirty minutes.

After the electrophoresis is complete, the gel is overlaid with stain consisting of 8 Phadebas amylase tablets dissolved in 10 ml of a 0.9% saline solution supplemented with 0.5% bovine serum albumin. The gel is maintained in a moist chamber at 56° C. for 2½ hr., and then the gel is rinsed in distilled water and soaked in distilled water for 5 minutes. The gel is then fixed in reagent grade ethanol for 2 hours. The fixed gels are rinsed briefly in distilled water.

To dry the gel, a sheet of blotter paper is applied over its surface. A glass plate is placed over the blotter paper, and a 1 kg weight is placed on the plate and left on the plate for 10 min. The procedure is repeated with a fresh sheet of blotter paper. Drying is completed by placing the blotted gel in a vented oven at 50° C. for 15 minutes.

To quantitate the bands, the gels are scanned using a Beckman CDS-200 densitometer set at a transmission mode to read at 600 nm. The individual peaks are calculated as a percentage of the total.

The FIGURE is a photograph of isoamylase electrophoresis gel prepared according to the above Example. It can be seen from the FIGURE that the $P_1$, $P_{1b}$, $P_2$, $P_3$, $P_4$, $S_1$, $S_2$, $S_3$, $S_4$ and $S_5$ bands are clearly separated.

Although the test has been described above in terms of a protocol in which the gels and the electrophoresis reagents are freshly prepared, the gels may be prepared and packaged in sealed pouches and the running buffer packaged as dry mixes of the component reagents. As such, the electrophoresis supplies may be sold as a kit to clinical laboratories where testing of samples can be conducted with very little advance preparation by the clinical technician.

The adaptability of preparation as a prepacked test and the clear separation of the isoamylase bands are major advantages of the invention. In particular, the clear separation of all clinically significant isoamylase bands by the method of the present invention is an important improvement over previously described electrophoresis techniques.

While the invention has been described in terms of a certain preferred embodiment, modifications obvious to one with ordinary skill in the art may be made without departing from the scope of the present invention.

Various feature of the invention are set forth in the following claims.

We claim:

1. An electrophoretic method of detecing human isoamylases comprising
    providing an aqueous buffer having a pH of between about 8.4 and about 9.2, said buffer consisting essentially of water, barbital anion at a concentration of between about 0.04 M and about 0.08 M, tris cation at a concentration of between about 0.03 M and about 0.07 M, sodium cation at a concentration of between about 0.03 M and about 0.07 M, said tris cation and said sodium cation being present in molar ratios of between about 0.5:1 and about 2:1, incorporating said buffer in an agarose gel of between about 0.4 and about 1.5 weight percent agarose,
    applying biological samples to said gel,
    subjecting said gel to a direct current electrical potential of between about 50 and about 400 volts and placing said gel in heat exchange relationship with a cooling block maintained at a temperature of between about 2° C. and about 25° C. so as not to denature the isoamylases or destabilize the gel, and
    developing said gel to reveal isoamylase bands,
    said method providing a clear separation of $P_1$, $P_{1b}$, $P_2$, $P_3$, $P_4$, $S_1$, $S_2$, $S_3$, $S_4$ and $S_5$ bands.

2. A method according to claim 1 including measuring the relative intensities of said developed isoamylase bands.

3. A method according to claim 1 wherein said developed isoamylase bands are measured by drying the gel and subsequently measuring the optical transmission of the gel in the region of the bands.

4. A method according to claim 1 wherein the pH of said buffer is between about 8.7 and about 8.9.

5. A method according to claim 1 wherein said gel is less than about 1 mm thick and each of said biological samples is applied in amounts providing amylase at levels of between about $5 \times 10^{-4}$ and about $4 \times 10^{-2}$ IU per cm of band length.

6. A method according to claim 1, said buffer containing calcium cation up to a concentration of about 0.002 M.

7. A method according to claim 1, said buffer containing lactate anion up to a concentration of about 0.002 M.

8. An electrophoresis plate for separating human isoamylases comprising a backing sheet and a gel on one surface of said sheet, said gel including an aqueous buffer with a pH of between about 8.4 and about 9.2, and consisting essentially of water, barbital anion at a concentration of between about 0.04 M and about 0.08 M, tris cation at a concentration of between about 0.03 M and about 0.07 M, sodium cation at a concentration of between about 0.03 M and about 0.07 M, said tris cation and said sodium cation being present in molar ratios of between about 0.5:1 and about 2:1, and agarose in amounts of between about 0.4 and about 1.5 weight percent of said gel.

9. A plate according to claim 8, said buffer containing calcium cation up to a concentration of about 0.002 M.

10. A plate according to claim 8, said buffer containing lactate anion up to a concentration of about 0.002 M.

11. A plate according to claim 8, wherein the pH of said buffer is between about 8.7 and about 8.9.

12. A prepackaged kit for effecting electrophoretic separation of human isoamylases comprising
    a dry mixture of tris barbital, barbital and sodium barbital which when added to a given volume of water provides an aqueous buffer with a pH of between about 8.4 and about 9.2, and said buffer consisting essentially of water, barbital anion at a concentration of between about 0.03 M and about 0.08 M, tris cation at a concentration of between about 0.03 M and about 0.07 M, sodium cation at a concentration of between about 0.03 M and about 0.07 M, said tris cation and said sodium cation being present in molar ratios of between about 0.5:1 and about 2:1, and
    a prepared agarose gel consisting of agarose at a concentration of between about 0.4 and about 1.5 weight percent and buffer of like composition to said aqueous buffer.

13. A kit according to claim 12 wherein said dry mixture includes calcium lactate so that said aqueous buffer contains calcium lactate up to a concentration of about 0.002 M.

14. A kit according to claim 12 wherein the pH of said aqueous buffer is between about 8.7 and about 8.9.

* * * * *